(12) United States Patent
Corazza et al.

(10) Patent No.: US 12,402,949 B2
(45) Date of Patent: *Sep. 2, 2025

(54) SYSTEM AND METHOD, FOR TRAINING AN INTERVENTIONALIST TO PERFORM AN INVASIVE PERCUTANEOUS INTERVENTION OR AN ENDOSCOPIC INTERVENTION

(71) Applicant: ADIS SA, Lausanne (CH)

(72) Inventors: Giulio Corazza, Morges (CH); Georges Caron, Echandens (CH); Hussein Ballan, St-Légier (CH)

(73) Assignee: ADIS SA, Lausanne (CH)

( * ) Notice: Subject to any disclaimer, the term of this patent is extended or adjusted under 35 U.S.C. 154(b) by 312 days.

This patent is subject to a terminal disclaimer.

(21) Appl. No.: 18/347,182

(22) Filed: Jul. 5, 2023

(65) Prior Publication Data
US 2025/0009430 A1 Jan. 9, 2025

(51) Int. Cl.
*A61B 34/10* (2016.01)
*G06T 7/246* (2017.01)

(52) U.S. Cl.
CPC .............. *A61B 34/10* (2016.02); *G06T 7/251* (2017.01); *A61B 2034/104* (2016.02); *G06T 2207/10028* (2013.01)

(58) Field of Classification Search
CPC .............. A61B 2034/104; A61B 34/10; G06T 2207/10021; G06T 2207/10028; G06T 2207/30021; G06T 2207/30241; G06T 7/251
See application file for complete search history.

(56) References Cited

U.S. PATENT DOCUMENTS 10,799,145 B2 * 10/2020 West .................. A61B 90/39
2022/0151701 A1 5/2022 Soler Arasanz et al.

FOREIGN PATENT DOCUMENTS

EP 4083769 A 11/2022

OTHER PUBLICATIONS

Korzeniowski et al., "VCSim3: a VR simulator for cardiovascular interventions," International Journal of Computer Assisted Radiology and Surgery, Springer, vol. 13, No. 1, 2017, XP036408464.
European Search Report for Application 23183652, dated Dec. 18, 2023, 10 pgs., European Patent Office, Germany.

* cited by examiner

*Primary Examiner* — Manuchehr Rahmjoo
(74) *Attorney, Agent, or Firm* — McDonald Hopkins LLC

(57) ABSTRACT

System for training an interventionalist to perform an invasive percutaneous intervention or an endoscopic intervention on an organ, by using a tool in this organ, where a merging unit is arranged for merging in real-time in a common environment a real-time 3D model of an end portion of a tool and a pre-computed 3D model of at least a portion of the organ. A display shows to the interventionalist the common environment, so that the interventionalist can see in real-time on the display where the real-time 3D model of this end portion of the tool is located with respect to the pre-computed 3D model of the portion of the organ, thus making the training of the interventionalist possible.

15 Claims, 5 Drawing Sheets

SYSTEM AND METHOD, FOR TRAINING AN INTERVENTIONALIST TO PERFORM AN INVASIVE PERCUTANEOUS INTERVENTION OR AN ENDOSCOPIC INTERVENTION

TECHNICAL DOMAIN

The present invention concerns an improved system and method, for training an interventionalist to perform an invasive percutaneous intervention or an endoscopic intervention on an organ of a human body or of an animal body ("organ" in the following), using a tool.

In particular, the system and method are improved since they take into account possible collisions between the real-time 3D model of the end portion of the tool with an inner wall of the virtual 3D model of the portion of the organ.

RELATED ART

Invasive percutaneous or endoscopic interventions, comprising minimally invasive interventions as for example a catheter ablation, on an organ using a tool are now routinely performed. During such interventions, an interventionalist (i.e. a physician specialized to perform invasive percutaneous or endoscopic interventions) inserts a tool into a body vessel of the patient's circulation or into another tubular system of the patient (for example, genitourinary tract, trachea and bronchi, or the gastro-intestinal tract) to get access to the target, i.e. the abnormality of the organ to be treated by the tool. Non limitative examples of such tools are catheters and guidewires, or devices like valves, or stents (to open a vessel) or coils to block a vessel (which e.g. supplies a tumor). The tools are substantially filiform. Their diameter is in the order of a few millimeters, typically three. Since body vessels are neither necessarily straight nor linear, those tools are flexible so that they can follow a path in the body vessel that includes torsions or deformations. Therefore, the tools must also be deformable.

During an invasive percutaneous or endoscopic intervention, once the tool has entered the body via a body vessel connected to the organ to be treated in the case of a percutaneous intervention or via a natural body entrance or body tube or tubular body cavity in the case of an endoscopic intervention (e.g. genitourinary tract, pulmonary system, gastro-intestinal tract), the interventionalist pushes the tool through this vessel or tube until it reaches the organ. Once the tool has entered the organ, the interventionalist uses the tool for treatment, for example by performing an ablation, taking a histological sample, placing a stent or deploying a device or coil. During the intervention, the interventionalist can move and deform the tool inside the organ.

Catheters are commonly used to treat the heart. For example, given state-of-the-art management techniques of patients with acute myocardial infarctions, an increasing portion of them survive this traumatic event. Unfortunately, some patients may develop inhomogeneous scar formations which are associated with malignant arrhythmias and sudden cardiac death.

To prevent this outcome, patients typically undergo electrophysiological testing followed by ablation of "semi-viable" heart scar tissue, also known as conduction channels, using a catheter. These interventions are performed by highly experienced electrophysiologists, but only 40% to 60% of patients are truly healed when treated with current state-of-the-art ablation techniques.

A contributing factor to this low success rate is that there currently exists no efficient training procedure that would allow interventionalists to practice for such invasive percutaneous interventions before actually performing them for real. This unmet need for training capabilities not only applies to heart interventions but also to interventions on other organs. This includes but is not limited to the brain, and angioplasty of many blood vessels, but also to interventions e.g. in the genitourinary system (prostate and other organs), the pulmonary system or the gastro-intestinal system (liver and other organs).

In the case of electrophysiological interventions, which is an example of an invasive percutaneous intervention, another contributing factor to this low success rate is the limited visualization of the target scar tissue provided by current voltage mapping techniques. Moreover, current voltage mapping techniques only allow for imperfect control of ablation lesion formation.

Document EP4083769, filed by the applicant and here integrated by reference, discloses a system for training an interventionalist to perform an invasive percutaneous or endoscopic intervention on an organ, by using a tool in this organ, comprises:

a pipe comprising an entrance and an exit and having a size and/or a shape similar to a body vessel or to a tubular body cavity, the body vessel and the tubular body cavity being connected to the organ, wherein the exit of the pipe physically simulates or represents the exit of the vessel or of the tubular body cavity at its junction with the organ;

this tool, arranged to be inserted by the interventionalist at the entrance of the pipe and to be pushed by the interventionalist through the pipe;

at least one stereoscopic camera arranged to acquire images of an end portion of the tool starting from the moment when this end portion starts emerging from the exit of the pipe;

a real-time 3D model generating unit, arranged for generating a real-time 3D model of this end portion of the tool from the images, a merging unit, arranged for merging in real-time in a common environment the real-time 3D model of the end portion of the tool and a pre-computed 3D model of at least a portion of the organ;

a display for receiving these data to show to the interventionalist this common environment, so that the interventionalist can see in real-time on the display where the real-time 3D model of the end portion of the tool is located with respect to the pre-computed 3D model of the portion of the organ, thus making the training of the interventionalist possible.

In this context, the term "vessel" indicates not only a blood vessel such as a vein or an artery, for example, it can be any other type of body vessel or a tubular body cavity, such as the urethra or other tubes that don't carry blood.

In this context, the expression "stereoscopic camera" indicates a camera comprising at least two sensors displaced with respect to each other so that they view substantially the same scene but from a different angle, thereby allowing a stereoscopic reconstruction.

In this context, the expression "real-time 3D model of the end portion of the tool" indicates that this 3D model changes over time. These changes can be captured at frame-rate given the images of the "real" (or "physical" or "concrete") tool that are acquired by the stereoscopic camera(s) while the interventionalist moves or deforms it during the simulated intervention. While training the user moves the tool and those images change over time, so that the corresponding 3D model changes as well. In other words, the real-time 3D model of the end portion of the tool is a video-based 3D model or a dynamic, as opposed to static, 3D model. For example, if the interventionalist manipulates the tool to move it or to deform it, then the 3D model, as shown on the display of the system according to the invention, will move or deform itself, respectively, in real-time so as to reproduce the actual tool motion or deformation, respectively, of the "real" tool as seen by the stereoscopic camera(s).

The system as described in the document EP4083769 has the advantage of delivering an immersive training system that will have a dual purpose. First, it will enable interventionalists to practice invasive percutaneous and endoscopic intervention on 3D models of organs for training purposes. Second, in a more operational context, it will help interventionalists to plan interventions before actually performing them.

The system as described in the document EP4083769 will make it possible to optimize the time, accuracy, and success rate of actual interventions. In the same way that flight training simulators cut down on pilot training costs, the system according to the invention will drastically reduce interventional costs by reducing interventional times at all levels through more thorough pre-operative planning.

Since by construction of the system as described in EP4083769 no collisions occur between the tool (which is as rod-like object) and the physical setup of the system, a problem of the system is to reconstruct the physical dynamics that the mentioned tool undergoes when interacting, and therefore colliding, with the pre-computed 3D (virtual) model of the portion of the organ, in particular with an inner wall of the pre-computed 3D (virtual) model of the portion of the organ.

Another problem of the system is to find a computationally efficient framework for simulating the physical evolution of the system given a minimal amount of input data. The solution must be realistic, and reliable.

There are several difficulties for which the above problem has not been tackled before, in particular the following difficulties:

The input can comprise n points in three dimensions parametrizing the centerline of the moving tool. In the minimal settings, no information is acquired on the causes of motion, nor on the internal stresses exerted on the material along the centerline. In particular, twist information regarding the internal rotations along the centerline may not be acquired.

Solving elastic equations with given boundary conditions is computationally expensive and far from feasible in real time simulations. Therefore, there is a computational speed issue to overcome.

The portion of the tool as seen by the stereoscopic camera(s) has a variable length in time, since it is moved by the interventionalist.

The complex shapes allowed for 3D virtual model of at least a portion of the organ can lead to a difficult determination of the collision response, in particular of the response direction.

Adequate approximations in integrating the information from the physical setup into the virtual simulation regarding the motion of the tool must respect the physical reliability of the model of the end portion of the tool.

SHORT DISCLOSURE OF THE INVENTION

An aim of the present invention is the provision of a system for training an interventionalist to perform an invasive percutaneous intervention or an endoscopic intervention on an organ, that overcomes the shortcomings and limitations of the state of the art.

Another aim of the invention is the provision of a system for training an interventionalist to perform an invasive percutaneous intervention or an endoscopic intervention on an organ, that takes into account possible collisions between the real-time 3D model of the end portion of the tool with an inner wall of the virtual 3D model of the portion of the organ.

Another aim of the invention is the provision of a system for training an interventionalist to perform an invasive percutaneous intervention or an endoscopic intervention on an organ, that is not computationally expensive. Another aim of the invention is the provision of a system for training an interventionalist to perform an invasive or minimally invasive percutaneous intervention or an endoscopic intervention on an organ, the system is computationally efficient and allows real time simulations with realistic hardware resources.

Moreover, the invention provides a possibility to plan minimally invasive procedures and according to the specific pathology and anatomy of the patient, test, practice and refine them on the inventive system before executing them on the patient.

According to the invention, these aims are attained by the object of the attached claims, and especially by the system for training an interventionalist to perform an invasive percutaneous intervention or an endoscopic intervention on an organ of claim 1, and by a method for training an interventionalist to an invasive percutaneous or endoscopic intervention on an organ of claim 15.

The system according to the invention for training an interventionalist to perform an invasive percutaneous intervention or an endoscopic intervention on an organ, by using a tool in this organ, comprises:

a pipe comprising an entrance and an exit and having a size and/or a shape similar to a body vessel or a tubular body cavity, the body vessel or the tubular body cavity being connected to the organ, wherein the exit of the pipe physically simulates or represents the exit of the vessel or of the tubular body cavity at its junction with the organ;

said tool, arranged to be inserted by the interventionalist at the entrance of the pipe and to be pushed by the interventionalist through the pipe;

at least one stereoscopic camera arranged to acquire images of an end portion of the tool starting from the moment when this end portion starts emerging from the exit of the pipe, a tool tracking module, arranged to output first set of coordinates of 3D points that defines the 3D position of a tool's centerline, with regard to the output of said pipe, based on said image, a real-time 3D model generating unit, arranged for generating a real-time 3D model of this end portion of the tool, a merging unit, arranged for merging in real-time in a common environment said real-time 3D model and a pre-computed 3D model of at least a portion of the organ;

a display for showing to the interventionalist said common environment, so that the interventionalist can see in real-time on the display where the real-time 3D model of the end portion of the tool is located with respect to the pre-computed 3D model of the portion of the organ, thus making the training of the interventionalist possible.

According to the invention, the system comprises a real-time re-computing position unit, arranged to receive the first set of coordinates and to output second set of coordinates of 3D points that define the 3D position of the tool's centerline, with regard to the output of said pipe, wherein the second set of coordinates is different from the first set coordinates if there is a collision between the real-time 3D model of the end portion of the tool with an inner wall of the 3D model of the portion of the organ, wherein the second set of coordinates describes a deformation of the real-time 3D model of the end portion of the tool after this collision, the second set of coordinates belonging to a space defined by the 3D model of the portion of the organ. In this way, the virtual model of the end portion of the tool stays inside the virtual organ.

The re-computing position unit is arranged to "recompute" since the system has already computed the first set of coordinates of the 3D points defining the 3D position of the tool's centerline.

With respect to what is known in the art, the system according to the invention takes into account possible collisions between the real-time 3D model of the end portion of the tool with an inner wall of the virtual 3D model of the portion of the organ. Advantageously, the system is not computationally expensive and allows real time simulations.

In one embodiment, the second set of coordinates is equal to the first set of coordinates, if there is no collision between the real-time 3D model of the end portion of the tool with an inner of the 3D model of the portion of the organ.

In one embodiment, the system comprises a non-transparent box preventing the interventionalist to see the tool during the training and/or for defining a physical environment having an optimized light and/or an optimized noise for the stereoscopic camera.

In one embodiment, the physical environment is an empty environment, so that no collisions occur between the tool and the empty environment.

In one embodiment, the real-time 3D model of the end portion of tool has a variable length overtime.

In one embodiment, the real-time 3D model generating unit is arranged to generate from the images taken by the stereoscopic camera a cloud of 3D points that denote the position of the end portion tool with regard to the exit of the pipe, wherein the tool tracking module is arranged to use the cloud of 3D points so as to output the first set of coordinates of 3D points, wherein the tool tracking module is arranged to interpolate the cloud of 3D points, so as to produce a curve in three-dimensions parametrized in arc length, e.g. by using cubic splines.

In one embodiment, on the basis of this curve, the tool tracking module is arranged to compute a framed curve, i.e. a curve with an associated rotation variable, e.g. an adapted zero-twist framing along a material parameter of the curve.

In one embodiment, the tool tracking module is arranged to include a dependency on the time variable for a set of discretization points of the framed curve, by assigning at each discretization point a particle and an orientation with a given position and/or rotation, and/or a given mass and/or inertia tensor.

In one embodiment, the tool tracking module is arranged to derive linear and angular velocities associated to every particle and framing along tool.

In one embodiment, the real-time re-computing position unit comprises an elasticity sub-unit (or position-based dynamics sub-unit), for simulating elastic properties of the tool. In one embodiment, the elasticity sub-unit is arranged for implementing the Cosserat-Kirchhoff theory.

In one embodiment, the elasticity sub-unit is arranged to receive the zero-twist framing from the tool tracking module.

In one embodiment, the real-time re-computing position unit comprises a collision sub-unit, for detecting a collision between the real-time 3D model of the end portion of the tool and an inner wall of the 3D model of the portion of the organ, and for generating collision constraints in the real-time 3D model of the end portion of the tool.

In one embodiment, the collision detection is performed by means of signed distance functions, which provide both a distance with the inner wall and a tool response direction.

In one embodiment, the real-time re-computing position unit comprises a feedback sub-unit, arranged to receive linear and angular velocities associated to every particle, from the tool tracking module and for integrating those velocities into the elasticity sub-unit, so as to take into account physical movements of the tool.

The invention concerns also a method for training an interventionalist to an invasive percutaneous or endoscopic intervention on an organ, by using a tool in this organ, comprising:

providing a pipe comprising an entrance and an exit and having a size and/or a shape similar to a body vessel or a tubular body cavity, the body vessel or the tubular body cavity being connected to the organ, wherein the exit of the pipe physically simulates or represents the exit of the vessel or of the tubular body cavity at its junction with the organ;

inserting said tool by the interventionalist at the entrance of the pipe and to be pushed by the interventionalist through the pipe;

acquiring by at least one stereoscopic camera, images of an end portion of the tool starting from the moment in which said end portion starts exiting from the exit of the pipe;

outputting by a tool tracking module, a first set of coordinates of 3D points that defines the 3D position of a tool's centerline, with regard to the output of said pipe, based on said image, generating by a real-time 3D model generating unit, a real-time 3D model of this end portion of the tool, merging by a merging unit, in real-time in a common environment said real-time 3D model and a pre-computed 3D model of at least a portion of the organ;

showing by a display to the interventionalist said common environment, so that the interventionalist can see in real-time on the display where the real-time 3D model of the end portion of the tool is located with respect to the pre-computed 3D model of the portion of the organ, thus making the training of the interventionalist possible.

According to the invention, the method comprises:

receiving by a real-time re-computing position unit, the first set of coordinates and outputting a second set of coordinates of 3D points that define the 3D position of the tool's centerline, with regard to the output of said pipe, wherein the second set of coordinates is different from the first set of coordinates if there is a collision between the real-time 3D model of the end portion of the tool with an inner wall of the 3D model of the portion of the organ, wherein the second set of coordinates describes a deformation of the real-time 3D model of the end portion of the tool after this collision, the second set of coordinates belonging to a space defined by the 3D model of the portion of the organ.

SHORT DESCRIPTION OF THE DRAWINGS

Exemplar embodiments of the invention are disclosed in the description and illustrated by the drawings in which.

Figure 8:
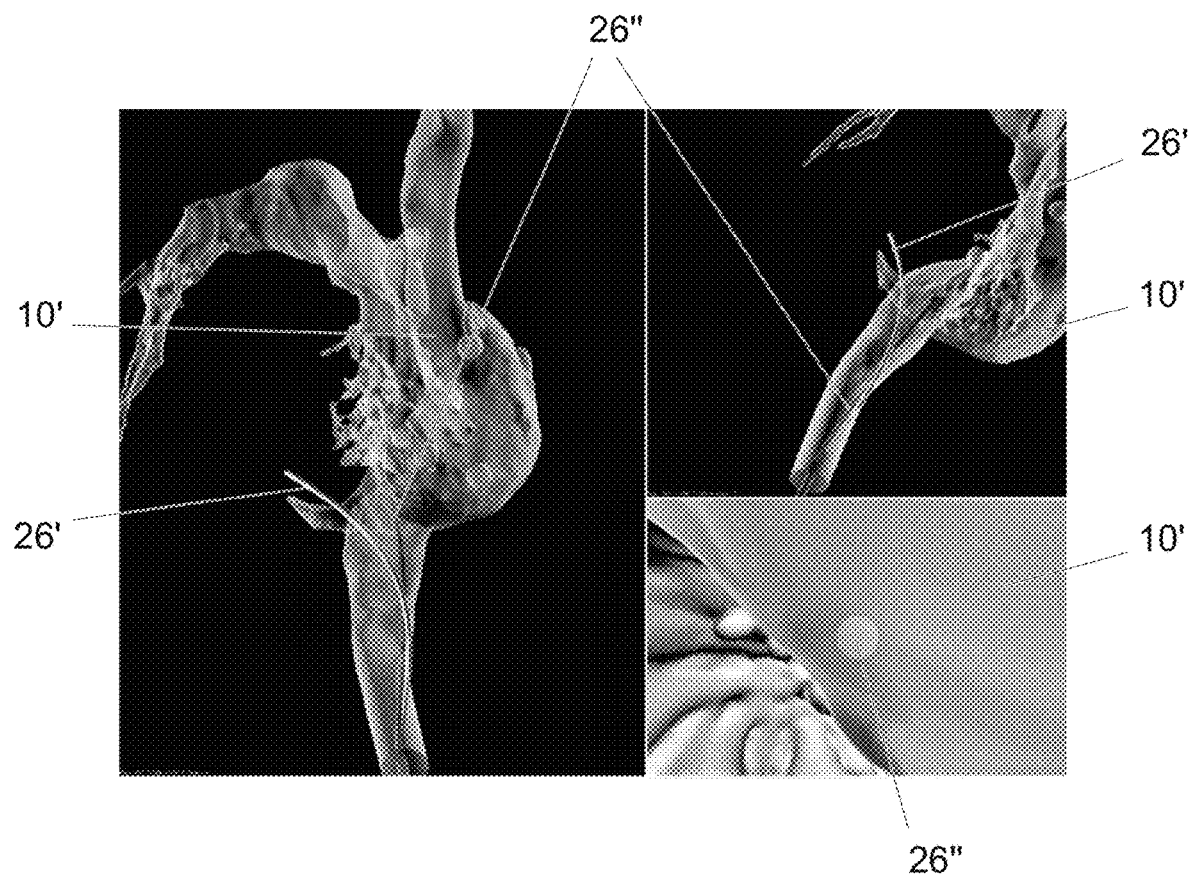

FIG. 8 illustrates different view of the resulting computations of the method according to an embodiment of the invention. The white tool is detected by the stereoscopic camera(s) and it is not constrained. Therefore, it freely moves beyond the boundaries. By contrast, the simulation output is represented by the grey tool, constrained to interact according to physical laws with the given virtual environment.

EXAMPLES OF EMBODIMENTS OF THE PRESENT INVENTION

Figure 1:
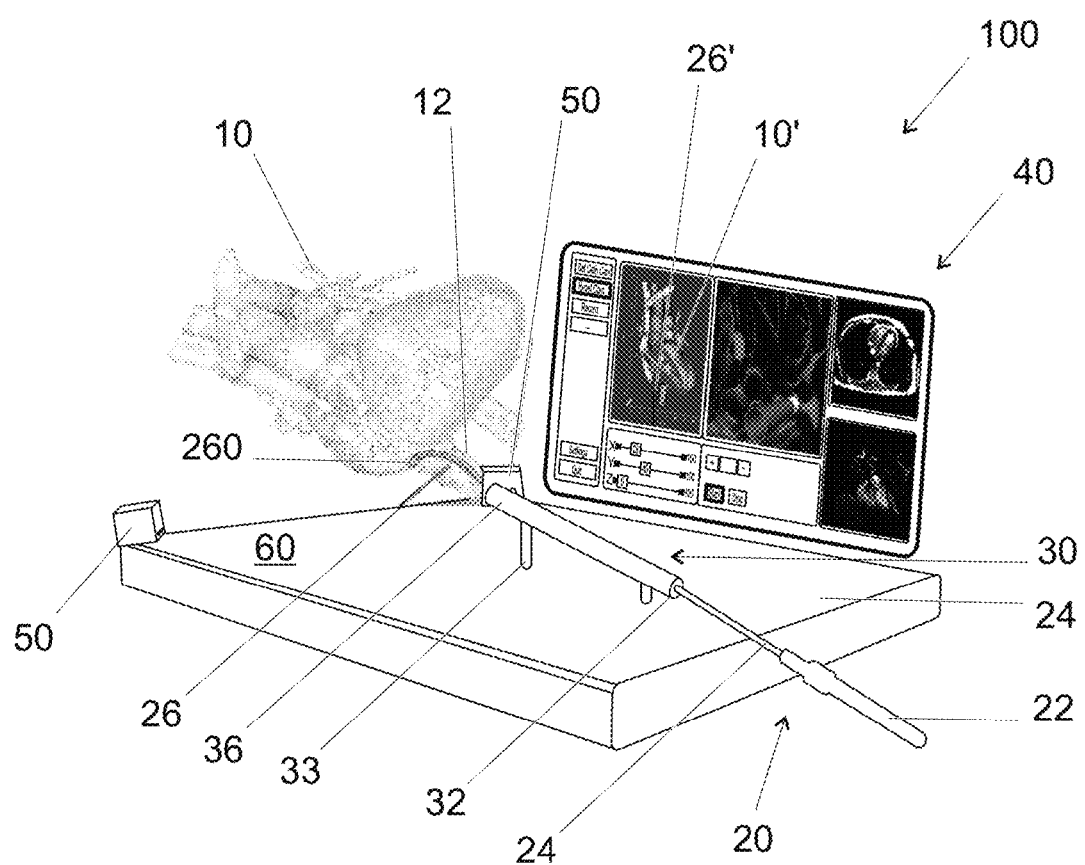
FIG. 1 illustrates a perspective view of one embodiment of the system according to the invention.

FIG. 1 illustrates a perspective view of one embodiment of the system 100 according to the invention. The system 100 can be used to train an interventionalist to perform an invasive percutaneous or endoscopic intervention on a physical organ, by using a tool 20 in the physical organ. The system 100 can also be used for planning interventions. Although FIGS. 1, 6, 7 and 8A to 8C depict the 3D model of a heart, the invention could also apply to the entire cardiovascular system (including vessels in any other body part) or other organ systems, such as the genitourinary system, the pulmonary system, or the gastro-intestinal system and others. While current endoscopic techniques can guide the tool to the organ to treat, the technique as described in this invention not only allows to guide the tool to the organ but once there, it allows to visualize the target even when embedded deeply in the organ and it allows to control the effect of treatment even for targets located deeply in the target organ.

The system 100 of FIG. 1 comprises a:
a pipe 30,
a tool 20, such as a catheter in the example of FIG. 1, arranged to be inserted by the interventionalist at the entrance 32 of the pipe 30 through an introducer sheet (not illustrated), which is located at the entrance 32 of the pipe 30,
two stereoscopic cameras 50,
a real-time 3D model generating unit and a merging unit not shown here,
a display 40.

The pipe 30 of the system 100 according to the invention comprises an entrance 32, an exit 36 and a body connecting the entrance 32 with the exit 36. According to the invention, the pipe 30 has a size and/or a shape similar or equal to the size and/or the shape of a vessel connected to the physical organ to be virtually operated on during a training session. In particular, the exit 36 of the pipe 30 simulates or represents the output of the vessel at a junction between the vessel and the organ.

The pipe 30 is intended to simulate a blood vessel, such as a vein or an artery, or any other tubular body cavity, such as the urethra or ureter and others (in the genitourinary tract), trachea and bronchi (in the pulmonary system), or the bile ducts and others (in the gastro-intestinal tract), through which an interventionalist can access to the organ to be treated using the tool 20.

In one embodiment, the pipe 30 is transparent, so that the interventionalist can see the movement of the tool 20 inside the pipe 30.

In one embodiment, the pipe 30 is made of a polymeric material, or of any other material presenting mechanical characteristics similar or equal to the mechanical characteristics of the corresponding physical vessel.

In one embodiment, the system comprises two or more pipes 30, connected to each other so as to form a ramified arrangement. This allows to simulate a ramified vessel, as one artery or vein separating into two.

In one embodiment, the diameter of the pipe 30 is similar or equal to the diameter of the corresponding physical vessel or other tubular body cavities.

In one embodiment, the length of the pipe 30 is similar or equal to the corresponding length of the vessel. In another embodiment, the pipe 30 is shorter than the corresponding physical vessel.

In one preferred embodiment, the pipe 30 is shorter than the tool 20, without its handle 22.

In one embodiment, pipe 30 contains a gel or a liquid simulating the physical properties of the liquid contained by the real vessel in the body, such as blood or urine. In one preferred embodiment, this substance is or comprises silicone. Hence, interventionalists receive the same haptic feedback when moving the tool 20 in the pipe 30, as if they were moving it in the body of a patient.

In the example of FIG. 1, the pipe 30 is supported by two feet 33 on a (substantially planar) base 60. However, the feet are not necessary. Moreover, only one foot can be present, as long as the stability of the pipe 30 on the base 60 is not compromised. The feet 33 of FIG. 1 have different heights, so that the pipe 30 is tilted with regards to the planar base 60. Since the system 100 illustrated in FIG. 1 comprises two stereoscopic cameras 50 on the base 60, which are equidistant from the output 32 of the pipe 30, this prevents having a dead angle when the stereoscopic cameras 50 acquire images of a portion of the tool 20, starting from the moment when it exits from the exit 36 of the pipe 30.

In another embodiment that is not illustrated, the system 100 comprises two stereoscopic cameras 50 on the base 60. They are equidistant from the exit 36 of the pipe 30, as the two stereoscopic cameras 50 of FIG. 1, and the pipe 30 lies on the base 60 or in a plane parallel to the base 60. This configuration guarantees that the epipolar lines of the two stereoscopic cameras will not be parallel and will eliminate any potential dead angles.

In another embodiment that is not illustrated, the pipe 30 lies on the base 60 or in a plane parallel to this base 60 and the system 100 comprises two stereoscopic cameras 50 on the base 60, which are equidistant from the exit 36 of the pipe 30, as the two stereoscopic cameras 50 of FIG. 1, and a third camera over the pipe 30 and forming with the exit 36 of the pipe 30 and the other two cameras a tetrahedron. This will be even more effective than the arrangement of 0043 at eliminating any potential dead angles.

Although in FIG. 1 there are two stereoscopic cameras 50, only one is required for the system 100 according to the invention to operate.

In one embodiment, the system comprises three stereoscopic cameras 50: this allows covering the entire vision of the tool 20.

In the example of FIG. 1, the tool 20 is a catheter. However, the tool 20 of the system 100 according to the invention can also be any other tool arranged to be inserted by the interventionalist at the entrance 32 of the vessel, so as to reach the organ. For example, and in a non-limiting way, the tool 20 can be a guidewire.

The tool 20 of FIG. 1 comprises a handle 22 arranged to be held by the interventionalist, so as to manipulate the tool 20, and, in particular, to insert it at the entrance of the pipe 30 and to push it through the pipe 30. It also comprises an end portion 26 and a body 24 between the handle 22 and the end portion 26. The end portion 26 comprises a free end 260.

In the illustrated example, the handle 22 has different diameters and its lowest possible diameter is smaller than the diameter of the main body 24 and of the end portion 26. In the illustrated example, the diameter of the main body 24 is equal to the diameter of the end portion 26. However, in other embodiments, those diameters can be different. For example, the diameter of the main body 24 can be smaller than the diameter of the end portion 26.

In one preferred embodiment, the tool 20 without its handle is longer than the pipe 30. Therefore, once the end portion 26 has been inserted at the entrance 32 of the pipe 30 and pushed by the interventionalist toward its exit 36, the free end 260 and then the end portion 26 of the tool 20 will eventually emerge from the exit 36 of pipe 30.

The flexible tool 20 is substantially filiform or rod-like. The diameters of the main body 24 and of the free end 26 are in the order of few millimeters, typically three millimeters. The tool 20 is flexible. It can be deformed, bended or twisted, so as to follow the shape of the body vessel, or the tubular body cavity and/or of the organ. For example, the end portion 26 of FIG. 1 is curved, so as to follow a curved path in the virtual organ 10.

In one embodiment, the system comprises a non-transparent box (not illustrated) preventing the interventionalist to see the tool 20 during the training and/or for defining a physical environment having an optimized light and/or an optimized noise for the stereoscopic camera(s) 50. The non-transparent box is placed, or it comprises the base 60. It defines a volume wherein at least the tool 20 and the pipe 30 are placed.

In one embodiment, the physical environment is an empty environment, so that no collisions occur between the tool 30 and the empty environment.

The system 100 according to the invention also comprises a real-time 3D model generating unit, not illustrated in FIG. 1. It is a computing unit designed to generate in real-time a 3D model of the terminal portion of the tool 20 starting from the time when it emerges from the exit 36 of the pipe 30 given the images acquired by the stereoscopic camera(s) 50, as the interventionalist deforms it during the simulated intervention. In other words, the real-time 3D model of the end portion 26 of the tool is a video-based 3D model or a dynamic, as opposed to static, 3D model.

In a preferred embodiment, the real-time 3D model generating unit comprises a real-time 3D model generating module, which is a machine learning-based module, i.e., a module that needs to be trained in order to progressively improve its performance on a specific task.

In a preferred embodiment, the real-time 3D model generating module is an artificial neural network, or network for short. Although a neural network is a preferred implementation of the machine-based learning module, the real-time 3D model generating module could be implemented using other machine learning techniques that can regress the 3D position of center line nodes of the flexible tool 20 from the output of the stereoscopic camera(s) 50. These include but are not limited to Gaussian Processes and Decision Forests.

In another embodiment, the real-time 3D model generating unit comprises no machine learning-based module. Instead, it is arranged so as to execute curve fitting algorithms.

The real-time 3D model of the end portion 26 of tool 20 changes over time, as it depends on the images taken in real-time of the "real" (or "physical" or "concrete") tool 20, as seen by the stereoscopic camera(s) 50. As the user moves the tool 20 in space so as to virtually treat the body organ, those images change over time and the corresponding 3D model changes as well. In other words, the real-time 3D model of the end portion 26 of the tool 20 is a video-based 3D model or a dynamic 3D model, as opposed to a static one.

As the user moves the tool 20 in space, the real-time 3D model of the end portion 26 of tool 20 has a variable length over time.

The real-time 3D model generating unit is connected to the stereoscopic camera(s) 50. The connection can be wired or wireless. It can be via internet, WLAN, mobile phone network, or any other wireless communication protocols and/or other communication techniques.

In one preferred embodiment, the real-time 3D model generating unit is a device distinct from the other devices of the system 100. However, in one embodiment, it could be, at least partially, be integrated in one of the other devices of the system 100, for example in the display 40 or in a stereoscopic camera 50.

In another embodiment, the real-time 3D model generating unit is at least partially integrated in a remote server.

The system 100 according to the invention also comprises a merging unit that is not illustrated. It may be a computing unit designed to merge in real-time into a common environment the changing real-time 3D model 26 of the tool 20 and a pre-computed 3D model of at least a portion of the target organ. It outputs the data representing this common environment.

The merging unit can be connected to the real-time 3D model generating unit, so as to form a computational pipeline. The connection can be wired or wireless. It can be via internet, WLAN, mobile phone network, or any other wireless communication protocols and/or other communication techniques.

In one preferred embodiment, the merging unit is a device distinct from the other devices of the system 100. However, in one embodiment, it could be, at least partially, integrated in one of the other devices of system 100, such as in the real-time 3D model generating unit, in the display 40, or in a stereoscopic camera 50.

In another embodiment, the merging unit is at least partially integrated in a remote server.

In one embodiment, the 3D model of the portion of the organ is a static 3D model, meaning that this 3D model does not change over time. In one embodiment, this static 3D model of the portion of the organ is generated by a machine learning-based module, named in the following "static 3D model generating module", that takes as input images from a Magnetic Resonance Imaging scanner, a CT scanner, or any other device able to generate volumetric images of organs.

In one embodiment, the 3D model of the portion of the organ is not static. In the real patient, many organs such as the heart move predominantly in feet-head direction during breathing. To simulate the respiratory motion of portion of the organ within the patient in the system 100, a feet-head motion can be added to the 3D model of the portion of the organ. This feet-head motion can follow simple sinus function, more complex functions, or can use respiratory motion patterns of a specific patient.

The static 3D model generating module can belong to a computing unit of the system 100, or to an external computing unit connected to the system 100.

According to the invention, the 3D model of at least a portion of the organ is "virtual", i.e. not real, e.g. it is not a solid 3D model like the one produced by a 3D printer.

In other words, the "real" organ is not present in the system 100 according to the invention. In fact, the organ 10 depicted as a heart in FIG. 1 is there for illustration purposes only. The interventionalist cannot see it when looking for example at the end portion 36 of the pipe 30. The interventionalist can only see the corresponding 3D (static) model 10' when looking at the display 40. On the display 40, the interventionalist can also see the real-time 3D model 26' of the end portion 26 of the linear tool 20, this real-time 3D model 26' being displayed in the 3D model 10' of (a portion of) the organ 10.

The merging unit is arranged to merge in a common environment both the real-time 3D model 26' and the static 3D model 10'. Moreover, the display 40 is arranged for receiving those data in order to display this common environment, so that the interventionalist sees on the display 40 the real-time 3D model 26' of the end portion 26 of the linear tool 20, which is displayed as placed in the (virtual) 3D model 10' of the portion of the organ 10, thus allowing the training of the interventionalist.

The displayed real-time 3D model 26' moves in the (virtual) 3D model 10' according to the movements of the real terminal or end portion 260 of the linear tool 20 as handled by the interventionalist and accounting for the virtual collisions. During the training, the interventionalist looks at the display 40, so as to learn and understand how to move the tool 20 so as to treat the organ.

In one preferred embodiment, the merging unit, before merging in the common environment both the real-time 3D model 26' and the (virtual) 3D model 10', performs a calibration step so as to align the position of an end 360 of the pipe 30, with the position of an entry portion of the (virtual) 3D model. In other words, the exit 36 of the pipe 30, which physically simulates or represents the end of the (real) body vessel (or of the real tubular body cavity) before it enters in the organ, is considered as a reference: the position of the free end 260 of the tool 20 as seen by the stereoscopic camera(s) is computed with regard to that reference.

Figure 2:
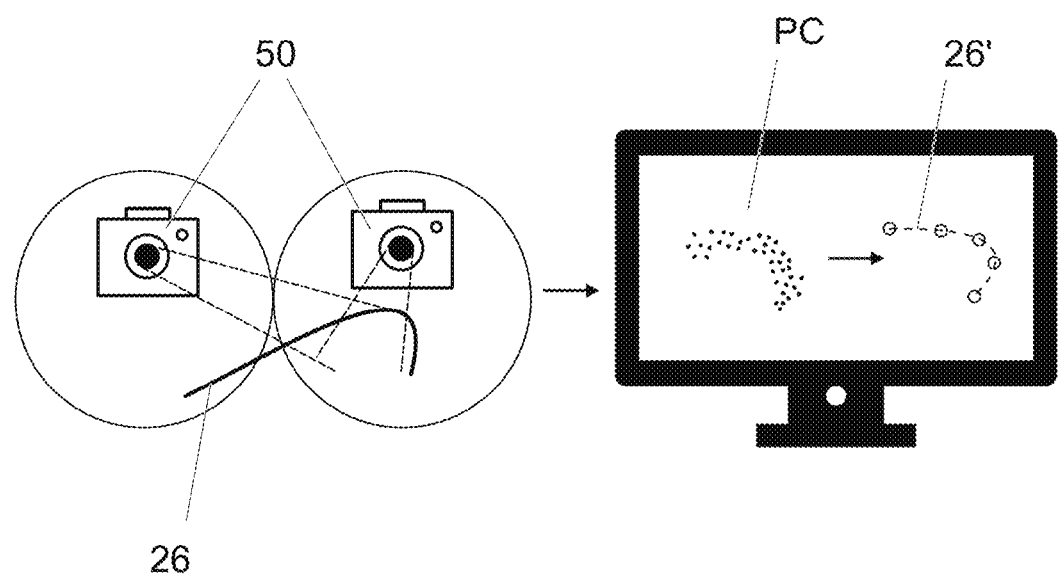
FIG. 2 illustrates a front view of a schematic embodiment of the system according to the invention.

FIG. 2 illustrates a front view of a schematic embodiment of the system 100 according to the invention.

The tool 20 is located in a pipe 30 and observed by one or more stereoscopic cameras 50 (FIG. 2 shows two cameras that give rise to a stereoscopic camera). The real-time 3D model generating unit is arranged to generate a cloud of 3D points PC, that denote the position of the tool 26, in particular, the position with regard to the exit 36 of the pipe 30.

In the example of FIG. 2, this cloud of 3D points is fed to a tool tracking module (not illustrated), which is a machine learning-based module, such as a neural network, arranged to output first set of coordinates of 3D points that define the 3D position of a tool's centerline, with regard to the output of the pipe 30, based on the images from the stereoscopic camera(s) 50. It is therefore possible to reconstruct a model 26' of the portion of the tool 20.

In one embodiment, the machine learning-based module outputs a grid of probabilities that the tool's centerline crosses the corresponding grid cells. That probability grid can then be thresholded to produce the binary occupancy grid, with ones where the tool 20 is and zero elsewhere. The same network also outputs a set of the 3D real-world coordinates of 3D points PC. These 3D points PC define the 3D position of the centerline of the tool's free end 260, with regard to the exit 36 of the pipe 30.

Figure 3:
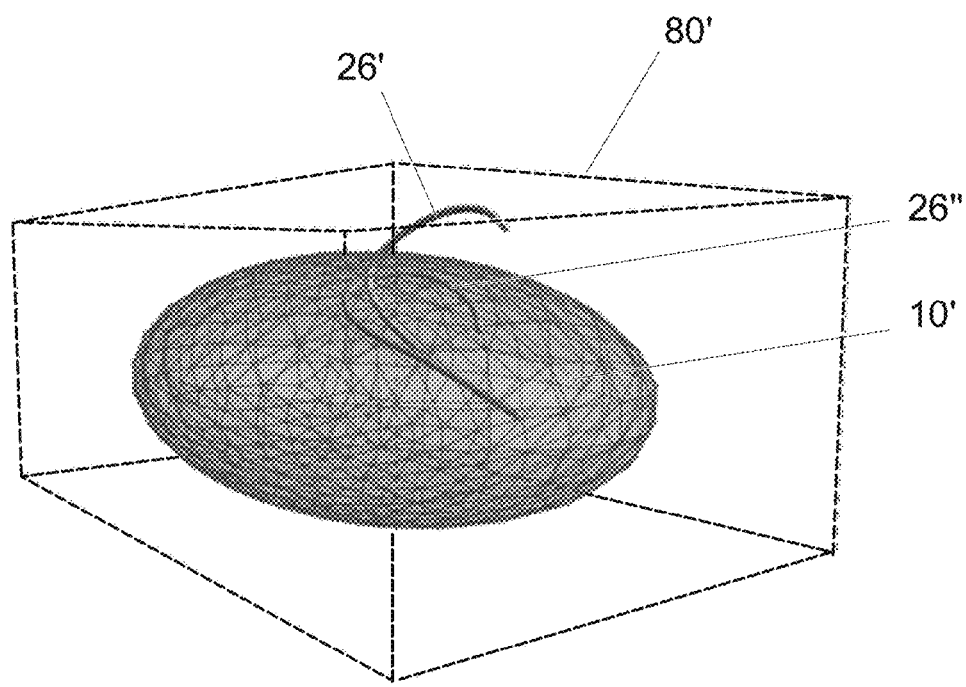
FIG. 3 illustrates a perspective view of a virtual 3D model of an organ, with the tool detected from the stereoscopic camera(s), freely moving in an empty space, and the same tool constrained to move and interact within the virtual 3D model of an organ.

FIG. 3 illustrates a perspective view of a virtual 3D model of an organ 10', with the model of the portion 26' of the tool, freely moving in the virtual environment 80', whose positions and/or movements correspond to the positions and/or movements of the physical portion 26 of the tool as detected by the stereoscopic camera(s) 50. Without the system 100 according to the invention, the collision of the model of the portion 26' of the tool with an inner wall of the portion of the virtual 3D model of the organ 10' is not taken into account, so that the portion 26' of the tool can exit from the virtual 3D model of the organ 10', by virtually crossing its inner wall.

FIG. 3 illustrates a perspective view of a virtual 3D model of an organ 10', with the virtual model of the portion 26" of the tool as computed by the system 100 according to the invention: the virtual model of the portion 26" of the tool is constrained to move and interact within the virtual 3D model of an organ 10'.

In conceivable variants of the invention, at least a portion of the tool 20 is modeled as a set of N nodes or points P, and a set of segments or curves linking the points. In one possible embodiment N is an integer number equal or higher than two. Setting N=4 allows to represent a (end) portion of the tool 20, this portion being 6 cm to 10 cm long. In one embodiment, the number of those nodes depends on the length of the tool. For example, the higher the number of nodes, the longer the tool. The tool tracking module produces a latent representation that is decoded into an occupancy grid 500. The position of the 3D nodes that define the 3D position of the tool's centerline is inferred from this latent representation.

In one embodiment, the system 100 comprises a tool tracking module, which is a machine learning-based module arranged to compute and/or track in real-time a position of the tool with regard to the exit 36 of the pipe 30.

In one embodiment, this tool tracking module belongs to the real-time 3D model generating unit. In another embodiment it belongs to another computing unit.

In one embodiment, this tool tracking module is arranged to detect the deformation and/or the torsion of the tool 20.

In one preferred embodiment, the tool tracking module is a deep neural network that learns an occupancy map and nodes or point P of the centerline CL belonging to a tool 20.

In one embodiment, a spatially optimized system of stereo cameras 50 is used for generating disparity images of a tool 20 allowed to move within an empty environment, such that no collisions occur between the object and the aforementioned environment. The generality of the setup allows the construction of virtual and complex scenarios where virtual collisions actually occur, which can be customized according to specific needs.

The system comprises also a display 40, visible in FIG. 1, for example, for showing to the interventionalist a common environment, so that the interventionalist can see in real-time on the display 40 where the real-time 3D model of the end portion of the tool 20 is located with respect to the pre-computed 3D model of the portion of the organ 10', thus making the training of the interventionalist possible.

As anticipated, a dense set of points in three-dimensions evolving through time (reference PC in FIG. 2) is generated from the disparity images from the stereo camera(s) 50 in order to describe the motion of the end portion 26 of the tool 20. In one embodiment, the physical system is designed to reduce the external noise and/or maximize the quality of the real-time collected data.

In one embodiment, the point cloud PC is stabilized and processed by means of the integration between specifically designed classical and artificial intelligence algorithms. In particular, a properly trained neural network reconstructs the skeleton of the centerline of the end portion 26 of the tool, to be used for further processing. Namely, the output comprises n three dimensional points evolving at real-time frame rate.

In one embodiment, at a given time, an input, i.e. a set of n three dimensional points approximating the centerline of the end portion 26 of the tool 20, is interpolated to produce a curve in three-dimensions parametrized in arc length (and therefore with an associated rest length). This can be done by using cubic splines with appropriate boundary conditions.

In one embodiment, on the basis of this curve, an associated adapted zero-twist (or natural) framing along the material parameter of the curve is computed.

In this context, a curve with a framing is called a framed curve, which is substantially a curve in the Euclidean space (with both position vector and rotation matrix) parametrized by a one-dimensional (material) parameter. The additional variables referring to the rotation matrices are necessary in order to apply a proper elastic rod theory.

Figure 4:
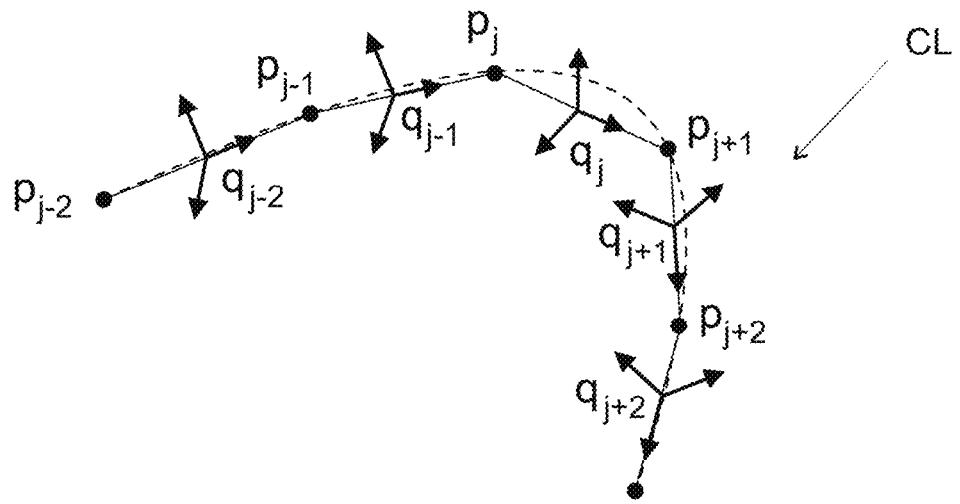
FIG. 4 is a schematic representation of the centerline at a given time of one embodiment of an end portion of a tool of the system according to the invention, wherein p denotes the position vector, q the quaternion parametrizing the rotation and the j index runs along the material parameter of the curve.

FIG. 4 is a schematic representation of the centerline CL at a given time of one embodiment of an end portion 26 of a tool 20 of the system 100 according to the invention, wherein p denotes the position vector, q the quaternion parametrizing the rotation and the j index runs along the material parameter of the curve.

In a possible optional variant, instead of a zero-twist framing along the material parameter, the same construction is made variable along the time (for each fixed value of the material parameter) in order to have a zero third component of the angular velocity of the end portion 26 of the tool 20. This avoids adding spurious information into the model.

It is important to emphasize that the construction of a twist minimizing framing is derived in an original manner and in the most computationally efficient formulation. Working in a discretized setting as shown in FIG. 4, and making use of quaternions q at the material parameter $s_j$ for parametrizing the rotations, one have:

$$q_{j+1} = \begin{pmatrix} 1+z & -y & x & 0 \\ -y & 1-z & 0 & x \\ x & 0 & 1-z & y \\ 0 & x & y & 1+z \end{pmatrix} q_j, \begin{pmatrix} x \\ y \\ z \end{pmatrix} := t_{j+1}, \quad (1)$$

where t is the unit tangent to the curve and the quaternions must be normalized after each iteration of the method.

In the framework of a variable-length end portion 26 of the tool 20, it is necessary to include a dependency on the time variable for the set of discretization points of the framed curve mentioned above.

In one embodiment, at each discretization point is assigned a particle with a given position in space and a given mass. The rotation variables are placed in the connecting edges and have an associated inertia tensor, see FIG. 4. At every time step, the length variation due to boundary inputs is modeled by adding new particles along the first tangent (elongation) or by deleting particles (shortening). This is performed at the boundary where the length-change of the end portion 26 of the tool 20. In one embodiment, the remaining particles which are not directly affected are instead shifted in space according to the following construction:

$$p_j \rightarrow p_j \pm (n \, l \pm l_c) t_0 \quad (2)$$

where p denotes the position of the particle, n the number of new/deleted particles, l the rest length discretization, $l_c$ the rest length correction due to boundary effects and finally to denotes the first tangent associated to the moving boundary. A positive sign is used in case of elongation, a minus sign in case of shortening.

In order to integrate the physical movements of the end portion 26 of the tool 20 into the virtual environment, in one embodiment collecting relevant data comprises applying a simple finite difference scheme for deriving the magnitude of linear and angular velocities associated to every particle and framing along the end portion 26 of the tool 20, on the base of the known positions and quaternions between two consecutive time stamps.

In a conceivable variant, using instead three consecutive time stamps, it is also possible to estimate the force and torque which generate the motion if any other force in the system is neglected. This last step depends upon the assigned masses and inertia tensors, which are indeed parameters of the model of the end portion 26 of the tool 20. Therefore, the above forces and torques are only proxies that describe the free motion of the particles disregarding elasticity, and can be used as an integrative information to stabilize and strengthen the algorithm.

In one embodiment, the elastic properties of the end portion 26 of the tool 20 are simulated by means of a position-based dynamics (PBD) approach which also takes into account the rotational degrees of freedom. Namely, a position-based dynamics implementation of the famous Cosserat-Kirchhoff elastic theory of rods is adopted. A possible reference for this theory is "Position and Orientation Based Cosserat Rods" by T. Kugelstadt and E. Schömer published in Eurographics/ACM SIGGRAPH Symposium on Computer Animation (2016).

In one embodiment, the choice of the present method for the elastic computations is based on the real-time speed constraint. On one hand, precise finite element methods and classical PDEs solver for elastic rod equations are orders of magnitude slower than actually needed. This is due to the highly non-linear nature of the Cosserat-Kirchhoff theory, which couples together the positional and rotational variables. In particular, the aim is to minimize an elastic energy depending on:

a) the so-called bending-twist strains, as a function of the difference with respect to the rest Darboux vector, and b) the stretching-compression-shear strains as a function of the difference with respect to the rest tangent and rotation.

Figure 5:
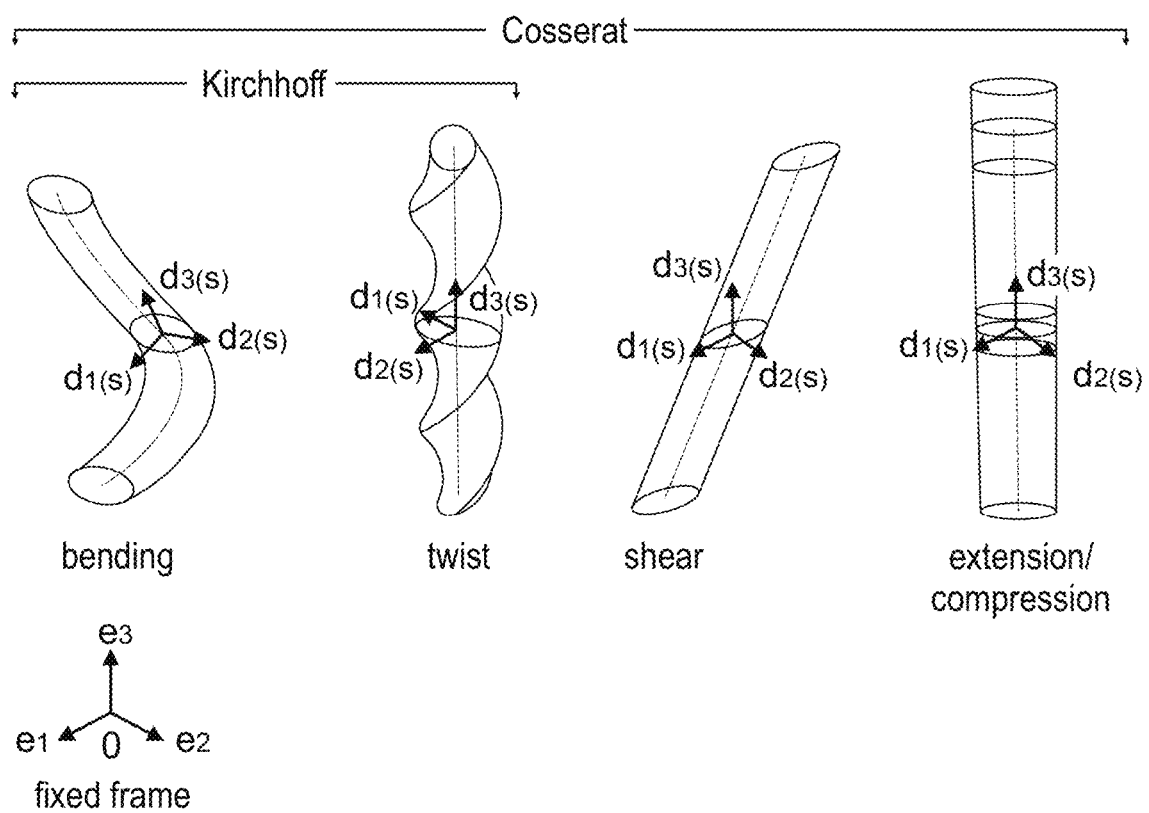
FIG. 5 is a description of the different degrees of freedom allowed by the Cosserat-Kirchhoff theory for the tool. Disregarding time, the directors $\{d_i\}$, as a function of the material parameters, provide the rotational degrees of freedom and are always represented with respect to a fixed orthonormal framing $\{e_i\}$.

FIG. 5 is a description of the different degrees of freedom allowed by the Cosserat-Kirchhoff theory for the tool. Disregarding time, the directors $\{d_i\}$, as a function of the material parameter s, provide the rotational degrees of freedom and are always represented with respect to a fixed orthonormal framing $\{e_i\}$.

In one embodiment, it is possible to restrict the degrees of freedom to the ones allowed by the Kirchhoff theory, namely only bending and twisting. This is done by implementing additional inextensibility and unshearability constraints. On the other hand, PBD (Position Based Dynamics) methods are extremely fast, reliable and represent a good approximation of the physical reality, minimizing the elastic energy using the strain measures from Cosserat theory as constraints that are iteratively enforced using a Gauss-Seidel solver to achieve the desired precision.

In one embodiment, the possible plastic behavior of the end portion 26 of the tool is taken into account. In this regard, "rest" quantities are present in its model. Specifically, these quantities play the role of reference variables for the elastic response, which is by definition the capability of a material to return back to the rest configuration after the application of a force and/or a torque. Namely the rest shape is usually characterized by a fixed length and time-independent strains. In the presented model instead the rest shape varies with time, and it is set to be the configuration of the simulated rod at the previous time step. This specification ensures that the end position 26 of the tool 20 correctly inherits the mechanical properties of the physical object when the deformation has a plastic nature.

The general skeleton of a PBD algorithm, in particular the one including the rotational degrees of freedom, being an important component for a proper elastic rod theory, is summarized here below. In the algorithm of the table here below, the expressions in italic characters indicate one embodiment of the method developed here; the expressions in normal characters indicate standard PBD steps. For more information on standard features of PBD methods, it is possible to refer to "Position Based Dynamics" by M. Müller, B. Heidelberg, M. Hennix, J. Ratcliff published in $3^{th}$ Workshop in Virtual Reality Interactions and Physical Simulations VRIPHYS (2006).

```
1: loop over time
   • a) Construct a zero-twist framed curve from the input
     b) Handle possible elongation or shortening as already described
     c) Derive the magnitude of linear and angular velocities
     return input
   • In case of interaction with the virtual environment (collision)
     return last variables
     end loop
2: for all particles do
     Initialize positions and velocities using last variables of loop 1
2: for all rotations do
     Initialize quaternions and angular velocities using last variables of loop 1
3: loop over time
   • Perform steps a), b) and c) as described above
   • Use step c) providing the physical velocities in order to constrain the magnitude of the
     simulated velocities accordingly
4: for all particles do
     If necessary, integrate the external force and update velocities and positions
5: for all rotations do
     If necessary, integrate the external torque and update angular velocities and
     quaternions
6: for all particles do
     • Perform collision detection and generate collision constraints
     • Specific collision detection and response for complex environments
     • Compute a proxy for the collision force
7: Update the reference configuration with the current configuration
8: loop over solver iterations
     Solve elastic constraints alternating the direction along the material parameter for
     enhancing the stability. Within the elastic constrains, a twist constrain and an exit
     direction constrain are developed specifically for the problem
     end loop
9: for all particles do
     Update linear velocities and return positions
10: for all rotations do
     Update angular velocities and return quaternions
```

In one embodiment, the collision detection with the virtual environment is performed by means of signed distance functions, which provide both the distance with the obstacle and the response direction via the gradient field. In particular, both continuous and static collision detection are used within the framework of position-based dynamics algorithms by application of adequate constraints. Restitution coefficients are also included in order to tune the velocity of a particle undergoing collision.

When the virtual environment is complex enough, collision detection and response can become problematic, especially for the determination of the response direction. This happens for example when the virtual shape presents highly non-convex patterns. In one embodiment, the directional variations of the gradient field around the end portion 26 of the tool 20 are detected, hence including additional information to the standard collision detection algorithm. Furthermore, a proxy for the colliding force can be estimated on the base of the elastic strains (deformations). This allows not only the visualization of the colliding particles and the associated impact force, but also to develop a reliable velocity damping scheme, to be coupled with more standard damping computations based on the average global motion of the end portion 26 of the tool 20.

Figure 6:
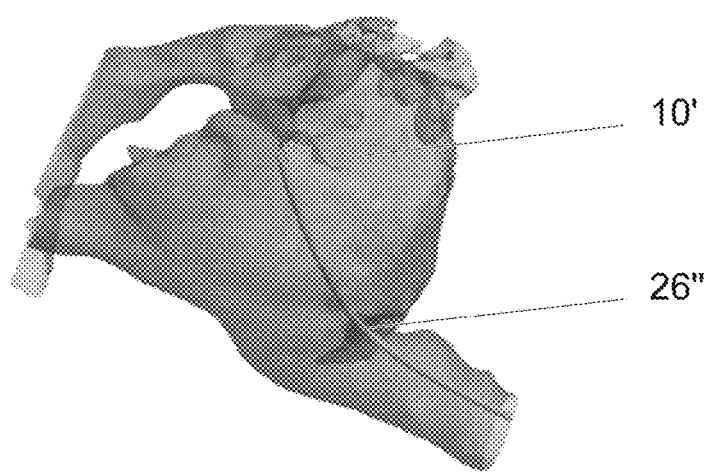
FIG. 6 illustrates a perspective view of a virtual 3D model of an organ, with the tool constrained to move and interact with the inner walls of the virtual 3D model of an organ and deforms according to physical laws.

FIG. 6 illustrates a perspective view of a virtual 3D model of an organ 10', with the end portion 26" of the tool constrained to move and interact with the inner walls of the virtual 3D model of an organ 10' and deforms according to physical laws.

Figure 7:
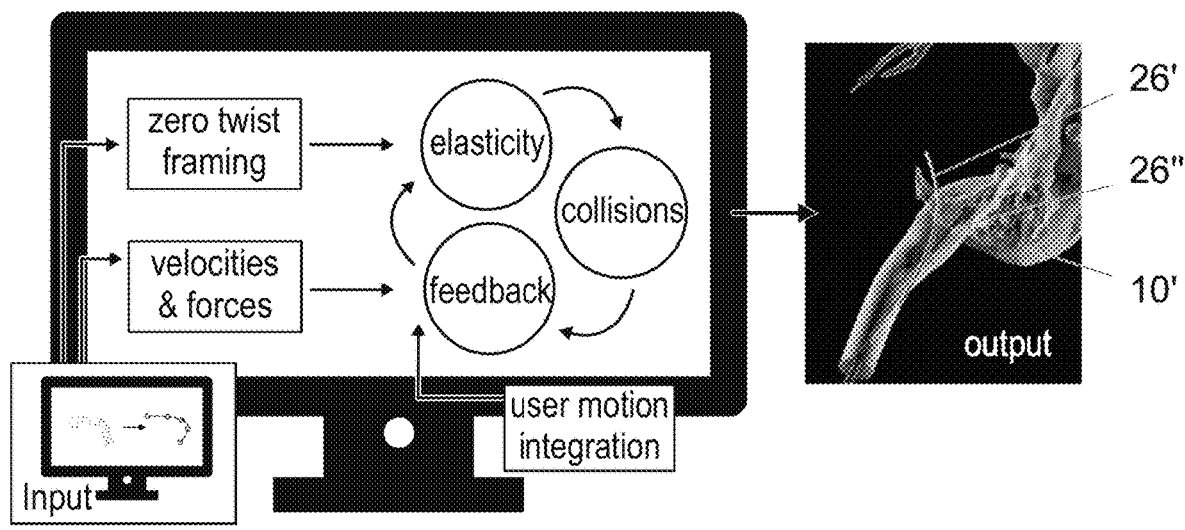
FIG. 7 is a schematic pipeline of the method according to an embodiment of the invention, together with the visualization of the resulting computations in a situation of interest on the right side.

FIG. 7 is a schematic pipeline of the method according to an embodiment of the invention, together with the visualization of the resulting computations in a situation of interest on the right side.

FIG. 8 illustrates different view of the resulting computations of the method according to an embodiment of the invention. The white end portion 26' of the tool is as detected by the stereoscopic camera(s) and it is not constrained. Therefore, it freely moves beyond the boundaries. By contrast, the simulation output is represented by the grey end portion 26" of the tool, constrained to interact according to physical laws with the given virtual environment.

In one embodiment, the initial number of particles (associated to t=0) is adapted to the initial length of the end portion 26 of the tool 20, such that the particle density throughout the simulation is independent of the initial data.

In one embodiment, dynamic and static friction is added to the model of the end portion 26 of the tool 20 by manipulating the tangential component of the velocities of the colliding particles.

In one embodiment, by tuning the masses and/or inertia tensors, it is possible to systematically constrain the movement of particles and framings. This is particularly useful to model boundary effects, or to assign specific rigidities to the rod-like object.

Since the length of the rod-like object is allowed to vary in time, some quantities, e.g., velocities and forces, must continuously undergo boundary interpolations to reach the necessary amount of data.

REFERENCE SIGNS USED IN THE FIGURES

10 Organ
10' Virtual 3D model of the organ
20 Tool
22 Handle of the tool
24 Body of the tool
26 End portion of the tool
26' Real-time 3D model of the end portion of the tool
26" Real-time 3D model of the end portion of the tool taking into account the response to a collision with an inner wall of the virtual 3D model of the organ
260 Free end of the tool
30 Pipe
32 Entrance of the pipe
33 Foot/support of the pipe
36 Exit of the pipe
40 Display
50 Stereoscopic camera
60 Planar base
80' Virtual environment
100 System
CL Centerline
CP point cloud
$d_i$ Directors as a function of the material parameter s
$e_i$ Fixed orthonormal framing
j Index
p Position vector
q Quaternion parametrizing the rotation
t tangent

The invention claimed is:

1. A system for training an interventionalist to perform an invasive percutaneous intervention or an endoscopic intervention on an organ, by using a tool in this organ, comprising:

a pipe comprising an entrance and an exit and having a size and/or a shape similar to a body vessel or a tubular body cavity, the body vessel or the tubular body cavity being connected to the organ, wherein the exit of the pipe physically simulates or represents the exit of the vessel or of the tubular body cavity at its junction with the organ;

said tool, arranged to be inserted by the interventionalist at the entrance of the pipe and to be pushed by the interventionalist through the pipe;

at least one stereoscopic camera arranged to acquire images of an end portion of the tool starting from the moment when this end portion starts emerging from the exit of the pipe;

a tool tracking module, arranged to output first set of coordinates of 3D points that define the 3D position of a tool's centerline, with regard to the output of said pipe, based on said image;

a real-time 3D model generating unit, arranged for generating a real-time 3D model of this end portion of the tool;

a merging unit, arranged for merging in real-time in a common environment said real-time 3D model and a pre-computed 3D model of at least a portion of the organ;

a display for showing to the interventionalist said common environment, so that the interventionalist can see in real-time on the display where the real-time 3D model of this end portion of the tool is located with respect to the pre-computed 3D model of the portion of the organ, thus making the training of the interventionalist possible, characterized in that the system comprises a real-time re-computing position unit, arranged to receive the first set of coordinates and to output second set of coordinates of 3D points that defines the 3D position of the tool's centerline, with regard to the output of said pipe, wherein the second set of coordinates is different from the first set of coordinates if there is a collision between the real-time 3D model of the tool with an inner wall of the 3D model of the portion of the organ, wherein the second set of coordinates describes a deformation of the real-time 3D model of the tool after this collision, the second set of coordinates belonging to a space defined by the 3D model of the portion of the organ.

2. The system of claim 1, wherein the second set of coordinates is equal to the first set of coordinates, if there is no collision between the real-time 3D model of the portion of the tool with the inner wall of the 3D model of the portion of the organ.

3. The system of claim 1, comprising a non-transparent box preventing the interventionalist from seeing the tool during the training and/or for defining a physical environment having an optimized light and/or an optimized noise for the stereoscopic camera.

4. The system of claim 2, the physical environment being an empty environment, so that no collisions occur between the tool and the empty environment.

5. The system of claim 1, the real-time 3D model of the end portion of tool having a variable length overtime.

6. The system of claim 1, wherein the real-time 3D model generating unit is arranged to generate from the images taken by the stereoscopic camera a cloud of 3D points that denote the position of the end portion of the tool with regard to the exit of the pipe,
wherein the tool tracking module is arranged to use the cloud of 3D points so as to output the first set of coordinates of 3D points,
wherein the tool tracking module is arranged to interpolate the cloud of 3D points, so as to produce a curve in three-dimensions parametrized in arc length, e.g. by using cubic splines.

7. The system of claim 6, wherein on the basis of this curve, the tool tracking module is arranged to compute a framed curve, i.e. a curve with an associated rotation variable, e.g. an adapted zero-twist framing along a material parameter of the curve.

8. The system of claim 7, wherein the tool tracking module is arranged to include a dependency on the time variable for a set of discretization points of the framed curve, by assigning at each discretization point a particle and an orientation with a given position and/or rotation, and/or a given mass and/or inertia tensor.

9. The system of claim 8, wherein the tool tracking module is arranged to derive linear and angular velocities associated to every particle and framing along the end portion of the tool.

10. The system of claim 9, the real-time re-computing position unit comprising a feedback sub-unit, arranged to receive linear and angular velocities associated to every particle, from the tool tracking module and/or for integrating those velocities into the elasticity sub-unit, so as to take into account physical movements of the end portion of the tool.

11. The system of claim 1, the real-time re-computing position unit comprising an elasticity sub-unit, for simulating elastic properties of the end portion of the tool.

12. The system of claim 11, the elasticity sub-unit being arranged to receive the zero-twist framing from the tool tracking module.

13. The system of claim 1, the real-time re-computing position unit comprising a collision sub-unit, for detecting a collision between the real-time 3D model of the end portion of the tool, and an inner wall of the 3D model of the portion of the organ, and for generating collision constraints in the real-time 3D model of the end portion of the tool.

14. The system of claim 13, the collision detection being performed by means of signed distance functions, which provide both a distance with the inner wall and an end portion of the tool response direction.

15. A Method for training an interventionalist to an invasive percutaneous or endoscopic intervention on an organ, by using a tool in this organ, comprising:
providing a pipe comprising an entrance and an exit and having a size and/or a shape similar to a body vessel or a tubular body cavity, the body vessel or the tubular body cavity being connected to the organ, wherein the exit of the pipe physically simulates or represents the exit of the vessel or of the tubular body cavity at its junction with the organ;
inserting said tool by the interventionalist at the entrance of the pipe and to be pushed by the interventionalist through the pipe;
acquiring by at least one stereoscopic camera, images of an end portion of the tool starting from the moment in which said end portion starts exiting from the exit of the pipe;
outputting by a tool tracking module, a first set of coordinates of 3D points that defines the 3D position of a tool's centerline, with regard to the output of said pipe, based on said image,
generating by a real-time 3D model generating unit, a real-time 3D model of this end portion of the tool,
merging by a merging unit, in real-time in a common environment said real-time 3D model of this end portion of the tool and a pre-computed 3D model of at least a portion of the organ;
showing by a display to the interventionalist said common environment, so that the interventionalist can see in real-time on the display where the real-time 3D model of the end portion of the tool is located with respect to the pre-computed 3D model of the portion of the organ, thus making the training of the interventionalist possible,
characterised in that the method comprises
receiving by a real-time re-computing position unit, the first set of coordinates and outputting a second set of coordinates of 3D points that defines the 3D position of the tool's centerline, with regard to the output of said pipe, wherein the second set of coordinates is different from the first set of coordinates if there is a collision between the real-time 3D model of the end portion of the tool with an inner wall of the 3D model of the portion of the organ,
wherein the second set of coordinates describes a deformation of the real-time 3D model of the end portion of the tool after this collision, the second set of coordinates belonging to a space defined by the 3D model of the portion of the organ.

* * * * *